United States Patent [19]

Malz, Jr. et al.

[11] 4,431,841

[45] Feb. 14, 1984

[54] PROCESS FOR MAKING DIARYLAMINES

[75] Inventors: Russell E. Malz, Jr., Naugatuck; Harold Greenfield, Watertown, both of Conn.

[73] Assignee: Uniroyal, Inc., New York, N.Y.

[21] Appl. No.: 419,249

[22] Filed: Sep. 16, 1982

[51] Int. Cl.$^3$ .............................................. C07C 85/00
[52] U.S. Cl. .................................................. 564/398
[58] Field of Search .......................................... 564/398

[56] References Cited

U.S. PATENT DOCUMENTS

| | | | |
|---|---|---|---|
| 2,513,132 | 6/1950 | Ballard et al. | 564/398 X |
| 2,947,784 | 8/1960 | Martin et al. | 564/398 |
| 3,138,640 | 6/1964 | Wilder | 564/398 X |
| 3,209,030 | 9/1965 | Bicek | 564/398 |
| 3,384,664 | 5/1968 | Schwettmann | 564/398 |
| 3,522,309 | 7/1970 | Kirby | 564/398 |
| 3,541,153 | 11/1970 | Sandridge | 564/398 |

*Primary Examiner*—Paul F. Shaver
*Attorney, Agent, or Firm*—Andrew D. Maslow

[57] ABSTRACT

An improved process for preparing diarylamines from alicyclic ketones, a primary aromatic amine, and a hydrogen acceptor, in the presence of a platinum metal catalyst and an acid promoter.

5 Claims, No Drawings

PROCESS FOR MAKING DIARYLAMINES

The invention relates to an improved process for making diarylamines by dehydrogenation of the reaction product of alicyclic ketones and primary aromatic amines. More particularly, the invention relates to an improved and economically practical method for forming compounds containing an aromatic radical linked to nitrogen and employing alicyclic ketones as a source of the aromatic radical.

It is known to produce arylamines from alicyclic ketones. U.S. Pat. No. 3,219,702 teaches a process in which a six membered alicyclic ketone is heated together with a hydrogen acceptor, a primary amine or amine precursor, and a dehydrogenation catalyst. Similarly, U.S. Pat. No. 3,219,703 teaches this process using a nitroaromatic as the hydrogen acceptor. U.S. Pat. No. 3,219,705 teaches the manufacture of N-cyclohexyl-N'-phenyl-p-phenylenediamine from cyclohexanone and a dehydrogenation catalyst. In all of the above patents the preferred catalyst is palladium.

A problem with the known process for making diarylamines from alicyclic ketones, aniline and nitrobenzene is that it requires the use of a costly amount of palladium catalyst.

It has been discovered that the addition of an acid promoter such as sulfuric acid, phosphoric acid, trihaloacetic acid or an alkyl or aryl sulfonic acid produces a marked improvement in the yield of the diarylamines in the process using palladium catalyst. It is not understood exactly why the yield is increased by the addition of an acid promoter and the result is unexpected and surprising.

According to the invention the acid promotion of the palladium catalyzed dehydrogenation of the reaction product of alicyclic ketones and primary aromatic amines produces diarylamines. A primary aromatic amine, a hydrogen acceptor, and an alicyclic ketone are heated with a palladium catalyst in the presence of an acid to produce a diarylamine.

Fundamentally, the process involves heating below decomposition temperature a primary aromatic amine, hydrogen acceptor and six membered alicyclic ketone with dehydrogenation catalyst. It is feasible to form cycloalkylideneamine as a preliminary independent step and then dehydrogenate by heating with catalyst, hydrogen acceptor and an appropriate acid. The temperature required for dehydrogenation is usually about the same. Dehydrogenation takes place without significant breaking of carbon-carbon bonds. Therefore, it will be understood that cycloalkylideneamine as starting material is essentially equivalent to primary amine plus alicyclic ketone.

Aromatization requires alicyclic ketones containing six carbon atoms in the ring of which one carbon is attached to the carbonyl oxygen, but substituents may be present in this ring and condensed ring compounds are suitable. These include cyclohexanone and tetralone, either of which may be substituted with $C_1$–$C_{12}$ alkyl groups, usually $C_1$ to $C_9$ alkyl groups. Examples comprise cyclohexanone, 2-methylcyclohexanone, 3-methylcyclohexanone, 4-methylcyclohexanone, 3,4-dimethylcyclohexanone, 2,4-dimethylcyclohexanone, 3,5-dimethylcyclohexanone, 2,5-dimethylcycohexanone, 2-ethylcyclohexanone, 4-ethylcyclohexanone, 2-propylcyclohexanone, 4-propylcyclohexanone, 4-isopropylcyclohexanone, 4-butylcyclohexanone, 4-tert-butylcyclohexanone, 4-octylcyclohexanone, 4-dodecylcyclohexanone, alpha-tetralone, beta-tetralone, 2-methyl-alpha-tetralone, 3-methyl-alpha-tetralone, 1-methyl-beta-tetralone, 4-methyl-beta-tetralone, 4-ethyl-alpha-tetralone, 5-methyl-alpha-tetralone, 6-methyl-beta-tetralone, 8-methyl-alpha-tetralone, 4-propyl-alpha-tetralone, 7-isopropyl-alpha-tetralone, 4-butyl-alpha-tetralone, 4-tert-butyl-alpha-tetralone, 2,3-dimethyl-alpha-tetralone, 2,4-dimethyl-alpha-tetralone, 4,8-dimethyl-alpha-tetralone, 4,5-dihexyl-beta-tetralone, 7,8-diethyl-alpha-tetralone, 4-nonyl-alpha-tetralone.

Any primary aromatic amine is suitable. Such arylamines may be substituted with one or more of the following: linear or branched alkyl groups of from one to twelve carbon atoms, alkoxy groups of from one to four carbon atoms, aryloxy groups of from six to fifteen carbon atoms, acyl groups of from one to twelve carbon atoms, aroyl groups of from seven to sixteen carbon atoms, amino groups, arylamino groups of from six to eighteen carbon atoms, alkylamino groups of from one to eight carbon atoms and dialkylamino groups of from two to sixteen carbon atoms. By way of illustration, there may be mentioned aniline, 1-naphthylamine, 2-naphthylamine, toluidine, 4-butylaniline, 4-tert-butylaniline, 4-dodecylaniline, 4-decylaniline, 3,4-dimethylaniline, 4-methoxyaniline, 4-ethoxyaniline, 4-tert-butoxyaniline, 4-aminodiphenyl ether, 4-(4'-nonylphenoxy)aniline, 4-aminoacetanilide, 4-benzoylaniline, 4-decanoylaniline, 4-(4'-nonylbenzoyl)aniline, 1,3 diaminobenzene, 1,4-diaminobenzene, N-phenyl-p-phenylenediamine, N-(4'-dodecylphenyl)-p-phenylenediamine, N-methyl-p-phenylenediamine, N-octyl-p-phenylenediamine, N,N-dimethyl-p-phenylenediamine, N,N-dioctyl-p-phenylenediamine.

Both mineral acids, such as sulfuric, phosphoric and hydrochloric acid, and organic acids, such as p-toluenesulfonic and trifluoroacetic, can be used as promoters. The preferred acid is sulfuric on the basis of cost and efficacy. The level of acid promoter is dependent on the concentration of reagents and catalyst, the diarylamine product made, the solvent, the purity of the materials and the desired cycle time. The mole % level of acid based on ketone may be from 0.05% to 10% or higher, with a preferred range 0.1% to 10% and a most preferred of 0.6% to 6%.

The catalyst in the present invention is a platinum metal and preferably palladium. Desirably, the dehydrogenation catalyst is supported on a carrier, preferably charcoal or alumina, most preferably charcoal. The catalyst usage is a major contributor to the cost of the process. The usage in our process is dependent on many parameters, including temperature, concentration of reagents, solvent, purity of materials, acid level, inhibitors generated during the reaction and cycle time.

Any of a wide variety of reducible materials may be used as hydrogen acceptor. The preferred hydrogen acceptors are nitrocompounds, as for example 2,6-dimethylnitrobenzene, m-tert-butylnitrobenzene, p-amylnitrobenzene, p-hexylnitrobenzene, p-octylnitrobenzene, p-sec.-octylnitrobenzene, p-tert.-octylnitrobenzene, p-nonylnitrobenzene, p-decylnitrobenzene, p-ethoxynitrobenzene, o-ethoxynitrobenzene, 2,6-dimethyl-4-aminonitrobenzene, nitrobenzene, p-dinitrobenzene, m-dinitrobenzene, p-dodecylnitrobenzene, 4-nitrodiphenyl, p-phenoxynitrobenzene, p-cyclohexylnitrobenzene, p-benzylnitrobenzene, nitromethane, nitroethane, 2-nitropropane, 1-nitropropane, 1-nitronaphthalene, 2-, 3- and 4-nitrotoluene, 4-nitroanisole, p-ethylnitrobenzene, p-propylnitrobenzene, p-isopropylnitrobenzene, m-ethylnitrobenzene, 4-nitrobenzonitrile, p-nitroacetanilide, p-nitroformanilide, 2,4-dinitrotoluene, 4-nitrobenzoic acid, m-butylnitrobenzene, p-tert.-butylnitrobenzene and nitrocyclohexane. The term "nitrocompound" is used in its usual sense to mean an organic compound containing an $NO_2$ radical. It is most advantageous to use as hydrogen acceptor a nitro compound which, when reduced to the corresponding amine serves as one of the starting materials, such as nitrobenzene in the production of diphenylamine. The concentration of nitro compound should be sufficient to act as hydrogen acceptor for stoichiometric amounts of Schiff base formed throughout the reaction. A minimum of ⅔ mole of nitrocompound per mole of ketone to be reacted is required in the case of cyclohexanone. Operation with excess amine is also feasible and has advantage in some instances. It then becomes desirable to recover the excess amine employed in the initial charge as well as any which may be formed during the reaction. As pointed out above, initial condensation between the amine and ketone may be carried out before the remainder of the reaction. After forming Schiff base by condensing ketone and primary amine, there is added ⅔ mole of nitrocompound per mole of Schiff base and the mixture heated in the presence of dehydrogenation catalyst and acid.

The reaction may be run in a closed system or at reflux with or without the removal of water. During the course of the reaction, the water which is evolved may be conveniently separated from the reaction mixture by employing an azeotropic distillation using solvents as benzene, toluene, xylene, cumene and p-cymene.

The aromatization may be run at temperatures as high as permitted by the stability of the reactants, intermediates, and products. The optimum temperature depends on the interaction of several parameters, including reactants, concentration of catalyst and acid, cycle time and solvent. While the temperature will usually be 70°–250° C., preferably 100°–200° C. these are not the absolute operating limits.

The ketone/nitrobenzene mole ratio may be in the range of 3/1–3/2, preferably 3/1–3/1.1. The hydrogen acceptor/primary aromatic amine mole ratio may be in the range of 1.1/2–1/2.2 and preferably 1/2. The amount of dehydrogenation catalyst, in particular palladium, may be in the range of 0.001–0.1 g, preferably 0.0025–0.075 g, most preferably 0.005–0.04 g of palladium, all per 100 mmoles of ketone.

The reaction may take place in the range of 1–48 hours but is preferably from 4–24 hours.

The following examples illustrate the invention in further detail.

EXAMPLE 1

Preparation of N-phenyl-1-naphthylamine (PANA)

To a 200 ml, 3-necked round bottom flask equipped with a thermometer and a Dean-Stark apparatus filled with p-cymene and having a condenser are added 7.45 g (80 mmole) of aniline, 4.82 g (39 mmole) of nitrobenzene, 14.6 g (100 mmole) of 1-tetralone and 65 ml of p-cymene solvent. Also introduced were catalyst and various acid promoters as indicated in Table I. The reaction mixtures were heated at reflux (about 185° C.) for 5 hours while removing the evolving water. Thereafter, the mixture was cooled to room temperature, and the catalyst was filtered out using a Celite (trademark) diatomaceous earth filter. The reaction mixture was analyzed by gas-liquid phase chromatography (GLPC) against a PANA standard. The yields mentioned in Table I are based on conversion of tetralone to PANA.

TABLE I

| Run No. | 1 | 2 | 3 | 4 | 5 | 6 | 7 | 8 |
|---|---|---|---|---|---|---|---|---|
| Palladium*, g | 0.01 | 0.01 | 0.02 | 0.03 | 0.04 | 0.01 | 0.01 | 0.01 |
| Acid: sulfuric, mmoles | 6 | 0.6 | 0.6 | 0.6 | 0.6 | — | — | — |
| phosphoric, mmoles | — | — | — | — | — | 6 | — | — |
| p-toluenesulfonic, mmoles | — | — | — | — | — | — | 6 | — |
| trifluoroacetic, mmoles | — | — | — | — | — | — | — | 6 |
| Yield PANA, mole % | 41 | 31 | 68 | 88 | 87 | 18 | 20 | 20 |

*Palladium catalyst charged as 5% palladium on carbon.

EXAMPLE 2

Using essentially the procedure of Example 1, 7.45 g (80 mmole) of aniline, 4.82 g (39 mmole) of nitrobenzene, 14.60 g (100 mmole) of 1-tetralone, 65 ml of p-cymene, and a 5% palladium on carbon catalyst were mixed and refluxed at about 185° C. for 5.0 hr. while removing the water of reaction with a Dean-Stark apparatus. The Dean-Stark trap was filled with extra p-cymene at the beginning of the experiment.

The results are shown in Table II below.

TABLE II

| Run No. | Catalyst wt., g. | 6N H$_2$SO$_4$ ml | milli-mole | 1-Tetralone % Recovered$^a$ | % Conversion | PANA Mole % Yield$^a$ | % Yield Based on tetralone Conv. |
|---|---|---|---|---|---|---|---|
| 9 | 0.20 | 0 | 0 | 73 | 27 | 0 | 0 |
| 10 | 0.20 | 0.2 | 0.6 | 4 | 96 | 88 | 92 |
| 11 | 0.20 | 2.0 | 6 | 28 | 72 | 73 | 101 |
| 12 | 0.60 | 0 | 0 | 75 | 25 | 7 | 28 |
| 13 | 0.60 | 0.2 | 0.6 | 0 | 100 | 78 | 78 |
| 14 | 0.60 | 2.0 | 6 | 7 | 93 | 81 | 87 |

$^a$Determined by quantitative glpc analysis. Yield of PANA calculated on basis that 1-tetralone is the limiting reagent.

The data demonstrate the improved yields obtained by the process of this invention.

EXAMPLE 3

Preparation of Diphenylamine (DPA)

Using essentially the same procedure as in Example 1, 7.45 g (80 mmole) of aniline, 19.7 g (160 mmole) of nitrobenzene, 19.6 g (200 mmole) of cyclohexanone and 65 ml of p-cymene were introduced in the flask as well as various amounts of palladium catalyst and sulfuric acid promoter as indicated in Table III. The % DPA yields are based on theoretical amount of DPA obtained from cyclohexanone.

TABLE III

| Run No. | 15 | 16 | 17 | 18 | 19 |
|---|---|---|---|---|---|
| Palladium, g | 0.01 | 0.05 | 0.01 | 0.01 | 0.05 |
| Sulfuric acid, mmoles | — | — | 0.6 | 0.6 | 3 |
| Reaction period, hrs. | 5.2 | 6.5 | 5 | 6 | 6 |
| DPA yield, mole % | 2 | 7 | 5 | 5 | 15 |

The results indicate that the process of this invention (use of combination of catalyst and acid promoter) unexpectedly at least doubles the yield obtained by using catalyst alone.

EXAMPLE 4

Preparation of N,N'-Diphenyl-p-phenylenediamine (DPPD)

To a 500 ml, 3-necked round bottom flask were added 92 g (500 mmole) p-aminodiphenylamine, 61 ml (600 mmole) cyclohexanone, 82 ml (800 mmole) nitrobenzene, 120 ml xylene solvent and 1.0 g of 5% palladium on carbon catalyst (0.05 g Pd). Using essentially the procedure of Example 1 the reaction was (A) carried out without acid and then again (B) in the presence of 3 millimoles of sulfuric acid. Reaction (B) provided about 40% (mole) more yield of DPPD over reaction (A) after 7 hours at reflux.

What is claimed is:

1. An improved process for preparing diarylamines from alicyclic ketones and primary aromatic amines, in the presence of platinum group catalyst, the improvement comprising carrying out the said process in the presence of an acid promoter selected from sulfuric acid, phosphoric acid, trihaloacetic acid, and alkyl or aryl sulfonic acid.

2. A process according to claim 1 wherein said primary aromatic amine is aniline.

3. A process according to claim 1 wherein said hydrogen acceptor is selected from the group consisting of nitrobenzene and nitrotoluene.

4. A process according to claim 1, 2 or 3 wherein said platinum group catalyst is palladium.

5. A process according to claim 4 wherein said acid promoter is sulfuric acid.

* * * * *